US007383197B1

(12) United States Patent
Neuman

(10) Patent No.: US 7,383,197 B1
(45) Date of Patent: Jun. 3, 2008

(54) METHOD AND APPARATUS FOR MATCHING CONSUMER OF HEALTH CARE SERVICES TO HEALTH CARE SERVICE PROVIDER

(76) Inventor: George G. Neuman, 20 Horse Hill Rd., Brookville, NY (US) 11545

( * ) Notice: Subject to any disclaimer, the term of this patent is extended or adjusted under 35 U.S.C. 154(b) by 420 days.

(21) Appl. No.: 09/625,420

(22) Filed: Jul. 25, 2000

(51) Int. Cl.
  *A61B 5/00* (2006.01)
(52) U.S. Cl. .............................. 705/3; 705/4; 128/920
(58) Field of Classification Search ............... 705/2–3, 705/4; 600/300; 707/100; 128/630, 920
  See application file for complete search history.

(56) References Cited

U.S. PATENT DOCUMENTS

| | | | |
|---|---|---|---|
| 5,301,105 A | | 4/1994 | Cummings, Jr. ............... 705/2 |
| 5,619,991 A | * | 4/1997 | Sloane ....................... 600/300 |
| 5,764,923 A | | 6/1998 | Tallman et al. ................ 705/3 |
| 5,772,585 A | * | 6/1998 | Lavin et al. ................ 600/300 |
| 5,845,254 A | * | 12/1998 | Lockwood et al. ............ 705/2 |
| 5,867,821 A | | 2/1999 | Ballantyne et al. ............ 705/2 |
| 5,890,129 A | | 3/1999 | Spurgeon ....................... 705/4 |
| 6,014,629 A | * | 1/2000 | DeBruin-Ashton ............ 705/2 |
| 6,151,581 A | * | 11/2000 | Kraftson et al. ................ 705/3 |
| 6,283,761 B1 | * | 9/2001 | Joao ........................... 434/236 |

* cited by examiner

*Primary Examiner*—Vanel Frenel
*Assistant Examiner*—Matthew S. Gart
(74) *Attorney, Agent, or Firm*—Ostrolenk, Faber, Gerb & Soffen, LLP

(57) ABSTRACT

A system to match a consumer of health care services to a health care service provider over a communications network, the system comprising at least one computer terminal associated with the consumer for allowing the consumer access to the communications network, a network server coupled to the communications network, the server comprising a computer program having, a service provider data base identifying a plurality of health care service providers and associated health care service products offered by the service providers, a first methodology for determining an appropriate treatment based on a diagnosis provided by the consumer or determined by an alternative diagnosis determiner, and a second methodology for determining at least one appropriate service provider based on a treatment preference comprising at least one of geographical location of the provider, insurance plan participation, cost, provider experience with the treatment and provider outcome with respect to the treatment.

48 Claims, 7 Drawing Sheets

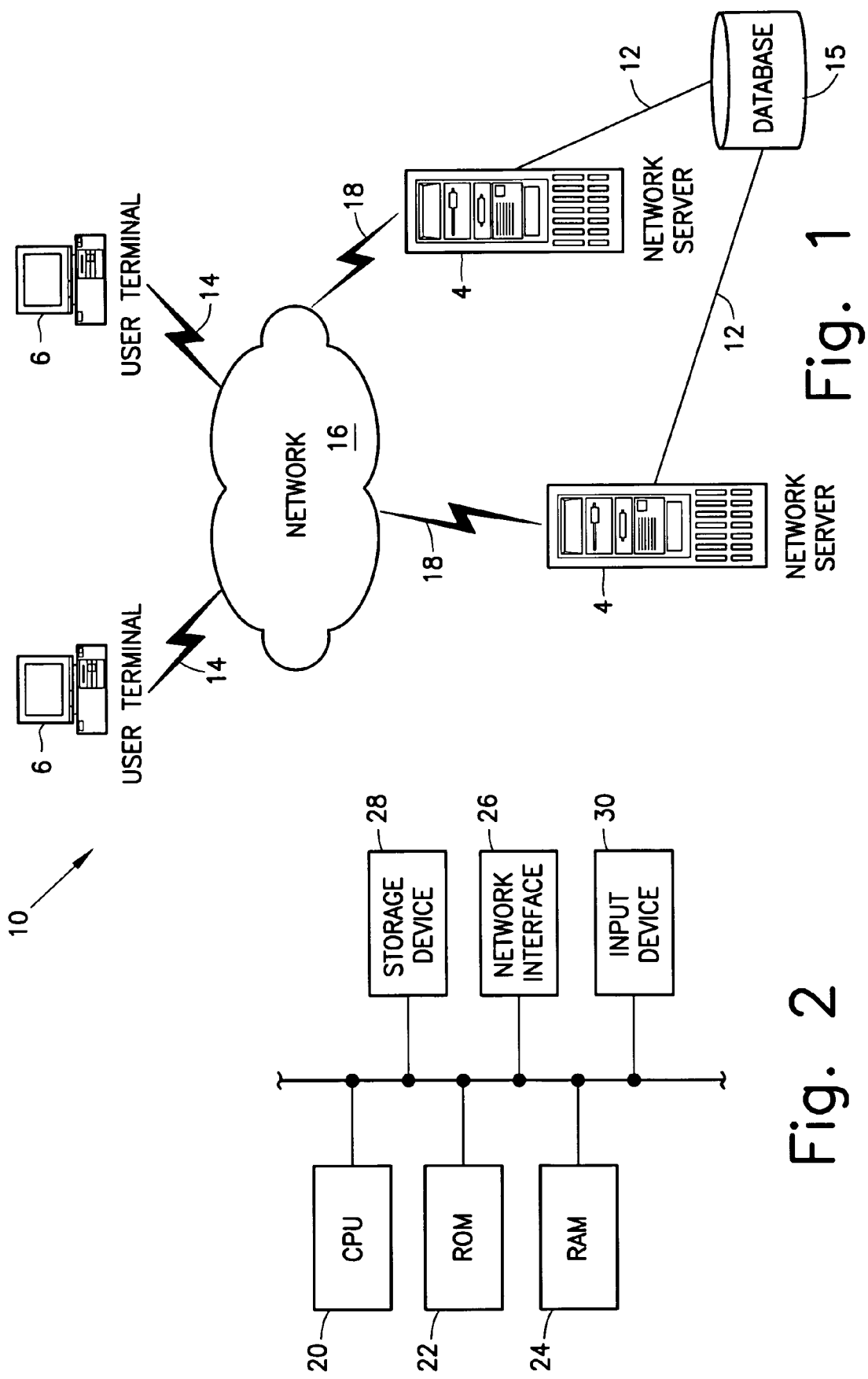

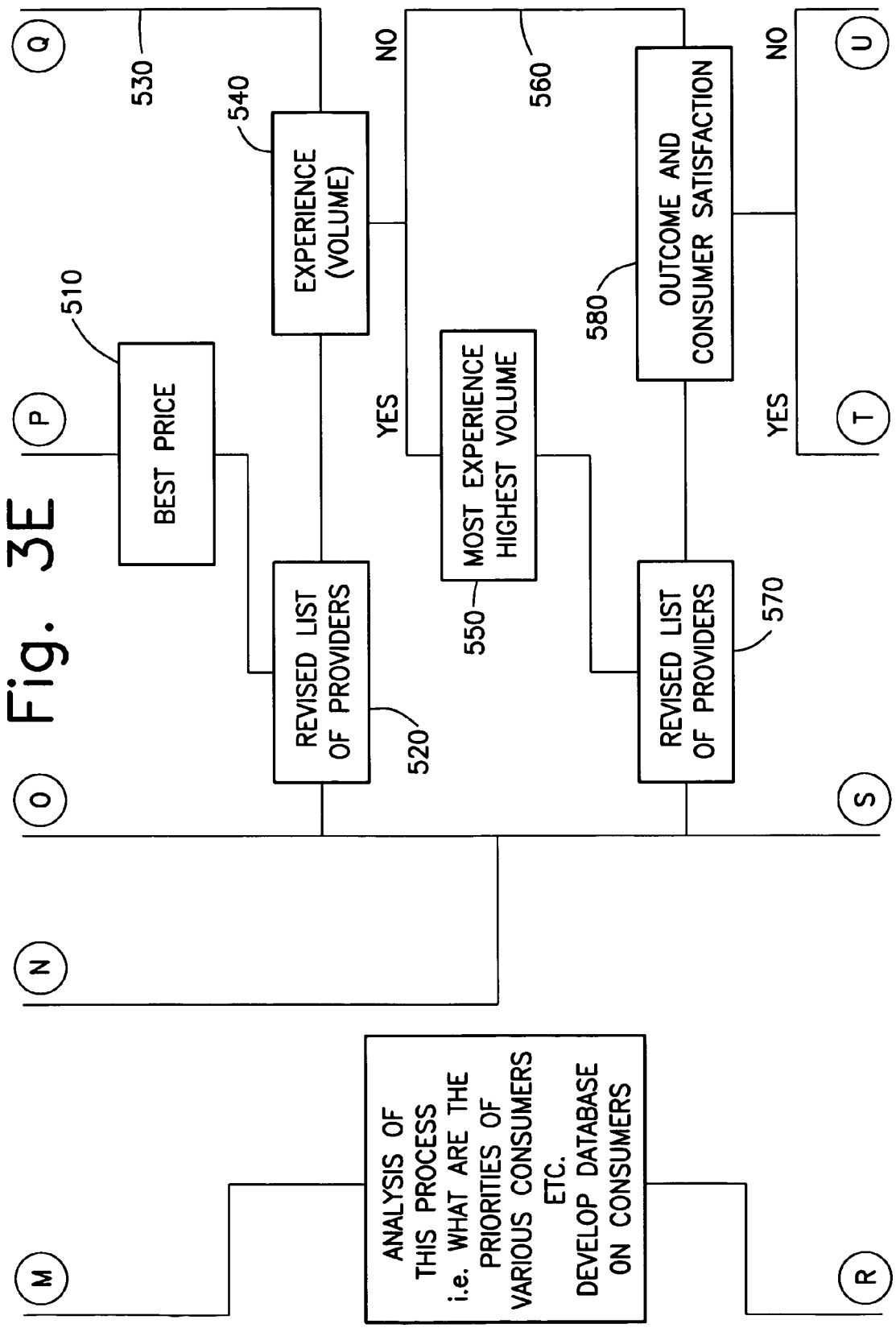

METHOD AND APPARATUS FOR MATCHING CONSUMER OF HEALTH CARE SERVICES TO HEALTH CARE SERVICE PROVIDER

BACKGROUND OF THE INVENTION

The present invention relates to a computerized system for obtaining medical services over a communications network, for example, the Internet. The present invention relates to a system which can be used by both individual patients and corporate consumers of medical services to determine who the appropriate provider of medical services for the consumer should be. The provider may be, for example, a particular hospital or physician. In particular, the present invention provides a method and apparatus to match a consumer of health care services to a health care service provider. The system of the invention can also be accessed by providers of medical services, for example, to update a database relating to medical services.

Various health care management systems are known. For example, U.S. Pat. No. 5,301,105 describes a health care management system. That system's stated aim is to integrate the "interconnection and interaction of the patient, health care provider, bank or other financial institution, utilization reviewer/case manager and employer so as to include within a single system each of the essential elements to provide patients with complete and comprehensive health care and payment therefor". See, col. 1, lines 55-60. Another known system is described in U.S. Pat. No. 5,890,129 which describes a system for exchanging health care insurance information between an insurer and multiple health care providers. Other known systems include U.S. Pat. No. 5,867,821 for a method and apparatus for electronically accessing and distributing personal health care information and services in hospitals and homes. This disclosed system is essentially a records management system. U.S. Pat. No. 5,764,923 discloses a medical network management system and process in which health plan beneficiaries access a team of health care professionals over the telephone to help assess their health needs and select appropriate care.

None of the prior art systems, however, allow for a consumer of medical health care services to be matched to a health care service provider over an automated communications network. The Tallman patent, U.S. Pat. No. 5,764,923 uses a telephonic system to help a team of health care professionals assess health needs and select appropriate care. The present invention represents an improvement over the prior art systems by using a communications network such as the Internet to allow a consumer to obtain medical health care services from an appropriate service provider.

SUMMARY OF THE INVENTION

The present invention relates to a system which allows the matching of a consumer of health care services to a health care service provider over a computerized communications network, such as the Internet. Although the Internet is shown as a typical communications network over which the invention can operate, the present invention is also applicable to other communications networks such as intranets, extranets, as well as proprietary communications networks.

The present invention relates generally to a system and process that allows the consumer to obtain health care services and the provider to market those services over the Internet. This e-commerce, service marketing tool, gives health care providers the ability to market any all-inclusive service (such as a diagnostic test) or package/global service (such as total joint replacement). It gives them the ability to change offerings and pricing depending on their current facility utilization, anticipated user volume etc. Presently there is no system or process that facilitates competitive marketing of health care services to the consumer. Excessive duplication of services and products exists in the health care marketplace. Managed care has failed in reducing health care costs. There has never been a free market in health care. Although the current climate for health care services is extremely competitive and the profit margins of health care providers are small, there is no service-marketing tool that brings the provider and the consumer together. Competitive marketing of health care services through e-commerce is an intrinsic element of the system. The Internet facilitates the matching of provider services with the consumer.

Provider services may be offered by health care organizations such as hospitals and medical centers, providers such as physicians, physicians' organizations, dentists, laboratories and other diagnostic and treatment facilities. Consumers include the public, both national and international, organized purchasers of health care services such as insurance companies, health maintenance organizations, corporations and providers such as hospitals who wish to outsource for certain services provided on their site.

The system allows providers to list the services they offer. Providers are preferably charged a fee to participate in this marketing service. For example, hospitals commonly devise global or package pricing for any number of procedures: High cost, high volume procedures such an orthopedic and obstetric; highly technical procedures such as organ and bone marrow transplants and open heart surgery; well defined medical conditions and surgical procedures such as cancer care. On a smaller scale, individual practitioners such as radiologists can market diagnostic studies such as MRIs and CAT scans; pain management specialists can treat back pain etc. Providers may elect to price their services according to anticipated volume usage. Global pricing benefits the consumer by allowing for improved availability of data, greater predictability of payers' costs, convenience and providing appropriate provider incentives.

The provider database will include general and detailed demographics as well as the experience of their organization with the particular service they are providing. The provider demographic database can be linked to other independent service data organizations that can provide specific information, i.e., outcome data, about the provider whether they be organizations or individuals. The provider will list the services or products it wishes to provide. These will be organized in a descriptive, alpha numeric, DRG, CPT, etc. format for later sorting and matching to consumers. The offerings will include specifics such as price, scope of the service, experience of the provider including outcome measures which may come from the provider or another validated database such as state, Medicare, JCAHO, IPRO, etc. statistics. These items form the foundation of the provider database. This database can be updated as frequently as desired by the provider. Pricing may be related to current utilization of the provider facility, for example if the cardiac surgery census is down, the global price may be reduced to encourage business.

Access to the program is provided to the consumer on a graduated cost basis ranging from no cost for individuals to increasing cost to corporate consumers based on the anticipated annual utilization. It is anticipated that providers will be motivated to reduce price as the volume of business increases. The process involved for the individual to match need to service is slightly more complicated than for an organization. A diagnosis or specific product need is necessary to utilize the service. If the consumer is uncertain of the diagnosis or service needed, the consumer is referred to a health care provider to establish the diagnosis. Once the diagnosis is established the consumer enters the Treatment Database. A specific diagnosis can yield one or more treatment options. These treatment options are listed and the consumer can explore each of those options further. Educating the consumer is an important benefit of this site. For example, the diagnosis of lower back pain, which has been diagnosed as lumbar disc inflammation, may have numerous treatment options including surgery, pain management, acupuncture, epidural steroid injection, etc. Validated treatment outcome data for each treatment option will be provided where feasible. The final treatment selection may then be established and the consumer can then access the Treatment Preference Database. This section of the system allows the consumer to match the treatment or health care product with the provider. The consumer can then prioritize various aspects of the desired service. These include: general demographics, cost, experience and outcomes (success statistics) of the desired service. The preferred list and access links are provided for the consumer to make contact with the provider. An access code is provided to each consumer to identify himself or herself to the provider. Follow up inquiries are e-mailed to all consumers to report their experience with providers. This information will be used to establish the Consumer Satisfaction Database concerning each individual provider. The follow-up inquiry will seek to establish the quality of the service provider from initial contact through conclusion of the service.

According to one aspect, the invention comprises a system to match a consumer of health care services to a health care service provider over a communications network, the system comprising at least one computer terminal associated with the consumer for allowing the consumer access to the communications network, a network server coupled to the communications network, the server comprising a computer program having: a service provider data base identifying a plurality of health care service providers and associated health care service products offered by the service providers, a first methodology for determining an appropriate treatment based on a diagnosis provided by the consumer or determined by an alternative diagnosis determiner; and a second methodology for determining at least one appropriate service provider based on a treatment preference comprising at least one of geographical location of the provider, insurance plan participation, cost, provider experience with the treatment and provider outcome with respect to the treatment.

According to another aspect, the invention comprises a method to match a consumer of health care services to a health care service provider over a communications network, the method comprising: allowing the consumer to access the communications network to connect to a network server coupled to the communications network, the server comprising a computer program having a service provider data base identifying a plurality of health care service providers and associated health care service products offered by the service providers, determining an appropriate treatment based on a diagnosis provided by the consumer or determined by an alternative diagnosis determiner; and determining at least one appropriate service provider based on a treatment preference comprising at least one of geographical location of the provider, insurance plan participation, cost, provider experience with the treatment and provider outcome with respect to the treatment.

According to still another aspect, the invention comprises a computer readable storage medium for a program for operating a system to match a consumer of health care services to a health care service provider over a communication network coupling at least one computer terminal associated with the consumer for allowing the consumer access to the computer network and a network server, the computer readable storage medium comprising a computer program comprising: a service provider data base identifying a plurality of health care service providers and associated health care service products offered by the service providers, a first methodology for determining an appropriate treatment based on a diagnosis provided by the consumer or determined by an alternative diagnosis determiner; and a second methodology for determining at least one appropriate service provider based on a treatment preference comprising at least one of geographical location of the provider, insurance plan participation, cost, provider experience with the treatment and provider outcome with respect to the treatment.

Other objects, features and advantages of the present invention will become apparent from the following description of the invention which refers to the accompanying drawings.

BRIEF DESCRIPTION OF THE DRAWINGS

The invention will now be described in greater detail in the following detailed description with reference to the drawings in which:

FIG. 1 is an overview of the hardware utilized by the system of the invention;

FIG. 2 is a block diagram of functional elements of a part of the invention; and FIG. 3, comprising FIGS. 3A to 3F, is an overview of the software which may be present on a communications network server or on some other device for implementing the invention.

DETAILED DESCRIPTION OF EMBODIMENTS OF THE INVENTION

Figure 3A:
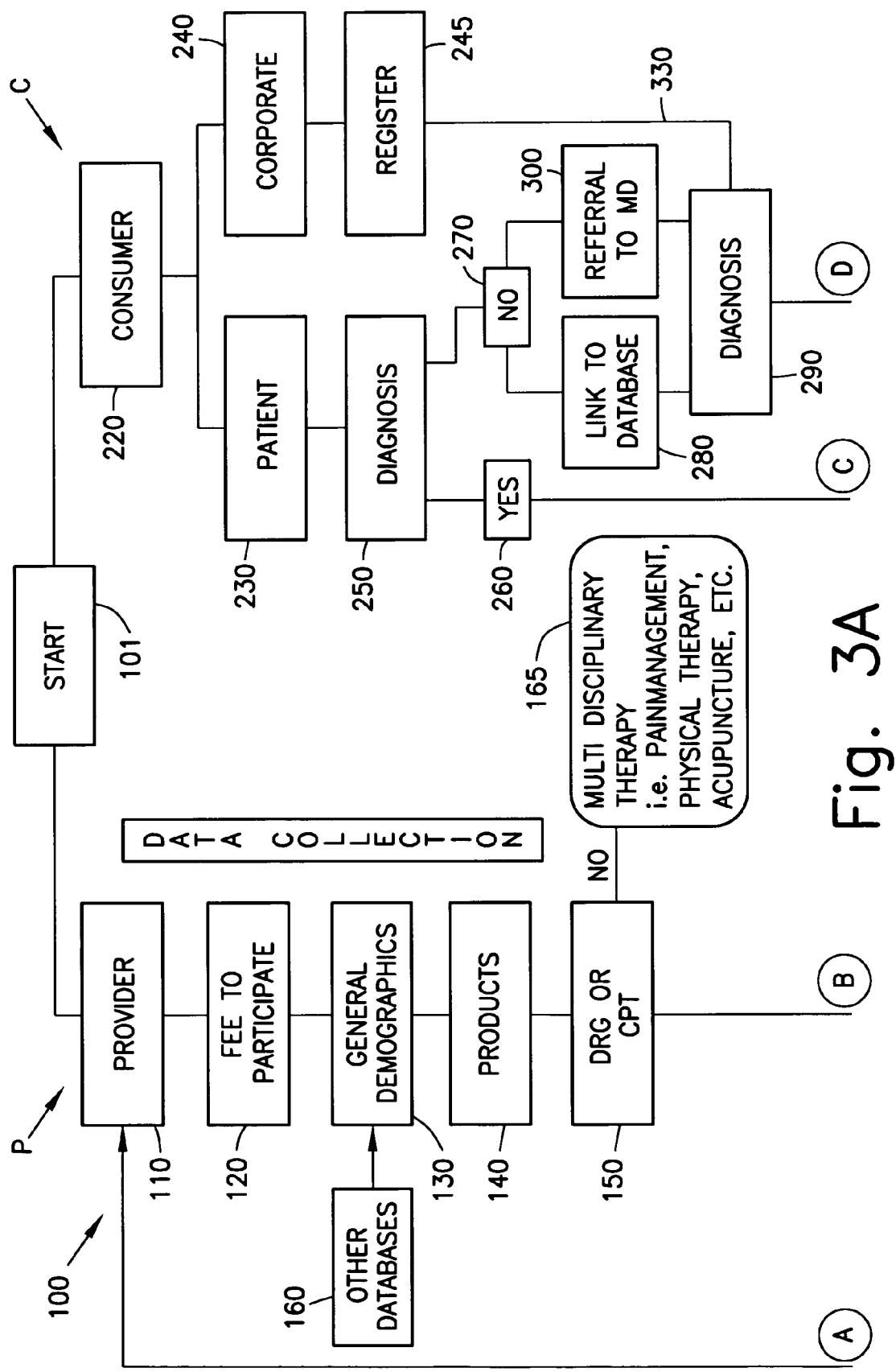

With reference now to the drawings, FIG. 1 shows a basic overview of the system of the invention.

FIG. 1 shows the hardware which can be used in the system according to the present invention. The system is comprised of one or more network servers 4 and one or more user terminals 6, for example, home or office computers. The network servers are arranged to communicate with database 15. The database 15 can be integrated within the physical housing of one or more of the servers 4 or can be a separate unit. If separate, database 15 can communicate with network servers 4 via connections 12 using any known communication method, including a direct serial of parallel interface over a local or wide area network. User terminal 6 communicates over data connections 14 to the network servers through communication network 16 via processor links 18. Communication network 16 can be any communication network but is preferably the internet or some other global computer network. Data connections 14 and processor links 18 can be any known arrangement for accessing communication network 16, such as dial-up, serial line interface protocol/point-to-point protocol (SLIP/PPP), integrated services digital network (ISDN), dedicated leased-line servers, broadband (cable) access, frame relay, digital subscriber line (DSL), asynchronous transfer mode (ATM) or other access technique.

User terminal 6 has the ability to send and receive data across communication network 16 and the ability to display the received data on a display device using the appropriate communications software such as an internet web browser. By way of example, terminals 6 may be personal computers such as Intel Pentium based computers or Apple, Macintosh computers, but are not limited to such computers. Other terminals which can communicate over a global computer network, such as palm top computers, personal digital assistants (PDAs) and mass marketed internet access devices, i.e., web TV, can be used.

According to the present invention, user terminal 6 accesses the network server 4 for the purpose of obtaining health care and, in particular, for matching the consumer of health care services to the appropriate health care provider. The network server 4 will access the database 15 in order to obtain information and perform operations pursuant to the program stored at the network server in order to determine the appropriate provider of medical care for the consumer.

As shown in FIG. 2, the functional elements of each network server, preferably include a central processing unit (CPU 20) used to execute software code in order to control the operation of the server, read only memory 22, random access memory RAM 24, at least one network interface 26 to transmit and receive data to and from other competing devices, such as user terminal 6, a storage device 28 such as a floppy disk drive, hard disk drive, tape drive, CD ROM. and the like for storing program code, databases and application data and one or more input devices 30 such as a keyboard and mouse.

The various components of the network servers 4 need not be physically contained within the same chassis or even located at a single location. For example, as explained above with respect to data base 15, which can reside on storage device 28, storage device 28 may be located at a site which is remote from the remaining elements of server 4 and may even be connected to CPU 20 cross communication network 16 via network interface 26. The nature of the invention is such that one of ordinary skill in the art of writing computer executable code (software) would be able to implement the described functions using one or a combination of popular computer programming languages such as "C++," Visual Basic, JAVA, HTML (hypertext markup language) or active -X controls and/or a web application development environment.

One of the functions performed by network server 4 is that of operating as a web site for the system for matching up healthcare service consumers with health care providers. A web site typically communicates with web browsers using the hypertext transfer protocol (HTTP) to send and receive data, including HTML web page data and executable JAVA applets. Of course, any known data transfer protocol and web site definition language can be used to implement the system.

As used herein, references to displaying data on a terminal refer to the process of communicating data to the terminal across network 16, and processing the data such that the data can be viewed on the terminal screen using an internet browser or the like. The display screen on user terminal 6 displays data which allows a user to "move" from website to website and even to display a composite image comprised of data gathered from multiple web sites. As such, each user's experience with the system will be based on the order with which the user progresses through, i.e., navigates, the various links. In other words, because the system is not completely hierarchal in its arrangement of display screens, users can proceed from site to site and area to area within each site without the need to backtrack through a series of display screens. For that reason, unless stated otherwise, the following discussion is not intended to represent any sequential steps, but rather a description of the components in operation of the system according to the invention.

Although the present invention is described by way of examples herein in terms of a web based system using web browsers and servers, the system is not limited to that particular configuration. It is contemplated that the system can be arranged such that user terminals 6 can communicate with and display data received from, the network servers 4 using any known communication and display method, for example, using a non-internet browser WINDOWS viewer coupled with a local area network protocol such as the internetwork packet exchange (IPX) protocol or a custom developed browser in a mobile cellular telephone coupled with a wide area networking protocol such as the wireless application protocol (WAP).

User terminals 6 maintain the same general configuration and function elements as network servers 4 with those elements sized for the expected usage and required performance of the devices. For example, user terminals 6 may have a CPU 20 which is of lesser capacity of that in servers 4 but may be additionally equipped with a sophisticated display then input device beyond those needed to support the operation of servers 4. Similarly, servers 4 may have storage device capabilities far in excess of that needed by user terminals 6. In addition, the links 18 coupling the network servers to the network 16 are typically high speed links and links 14 are lower capability links. However, the links 14 could be high speed links like the links 18.

It should be noted that the arrangement of the network servers and data base 15 allow the present invention to be scaled to accommodate large numbers of users and user terminals 6.

According to this arrangement, the network servers 4 provide the actual web interface to user terminal 6 while data base 15 maintains information relevant to user and healthcare service providers. However, as discussed, the database 15 need not be separate from servers 4. The database 15 can be integrated with the application software in servers 4.

Figure 3B:
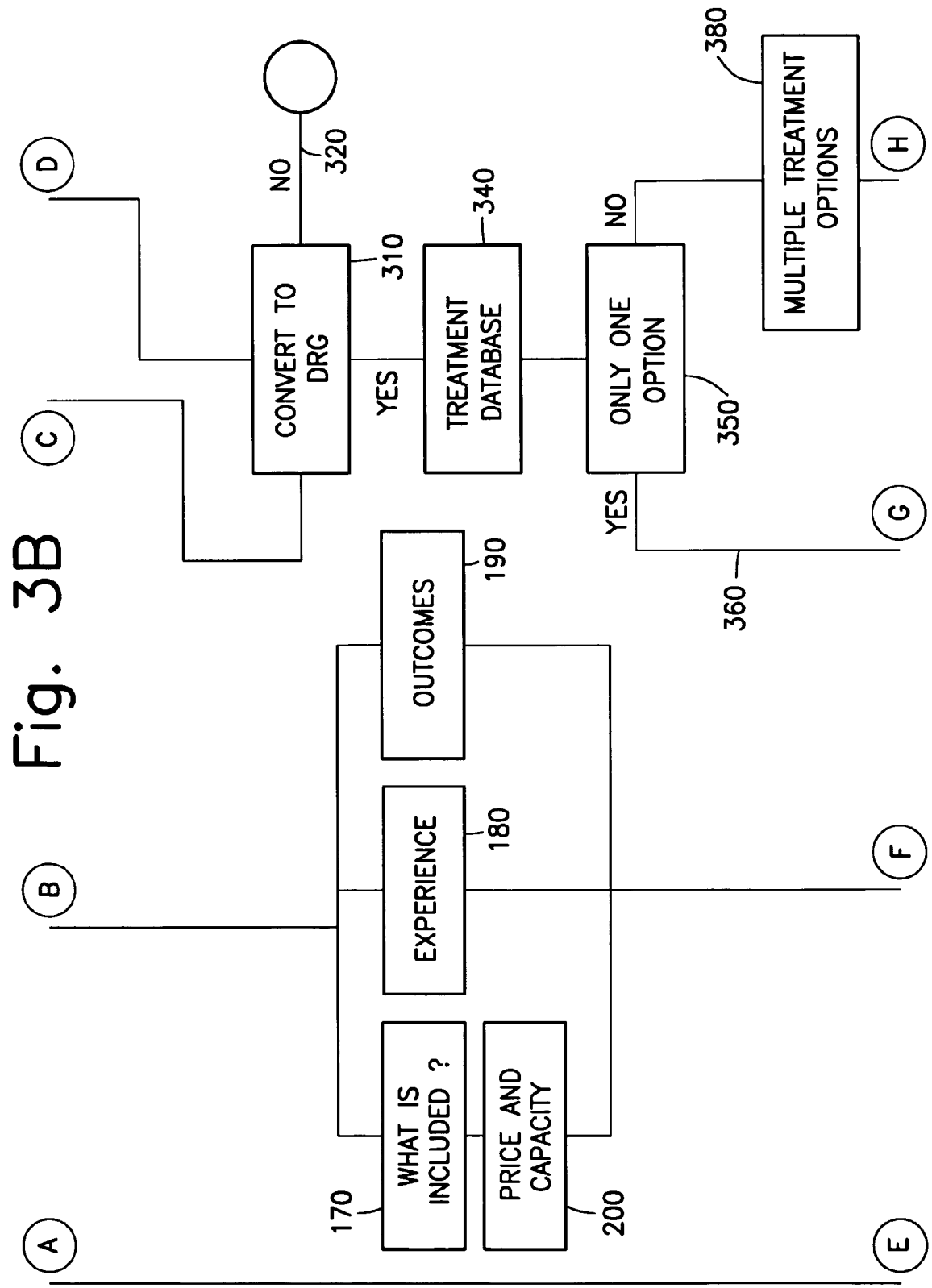
Figure 3C:
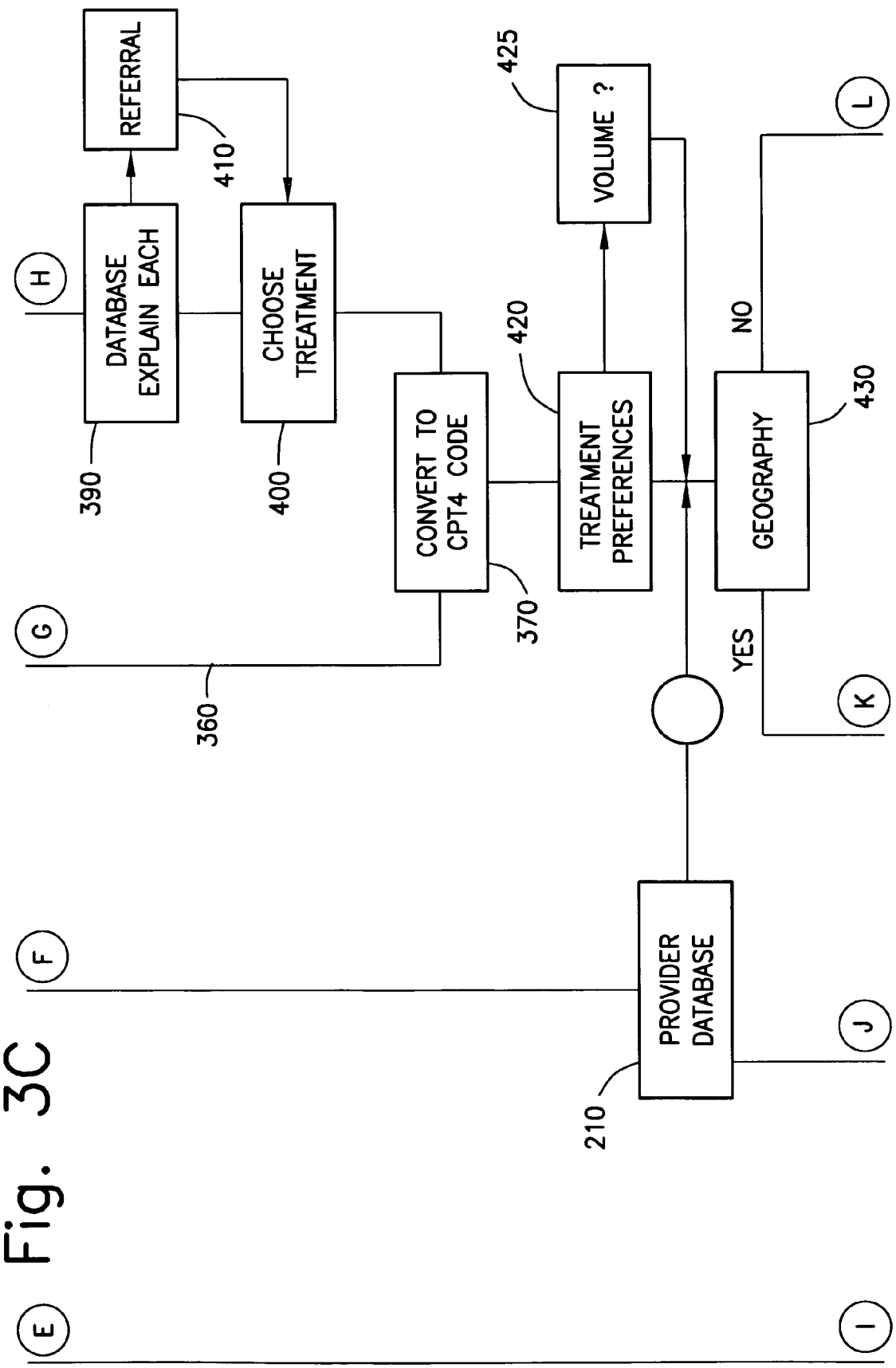
Figure 3D:
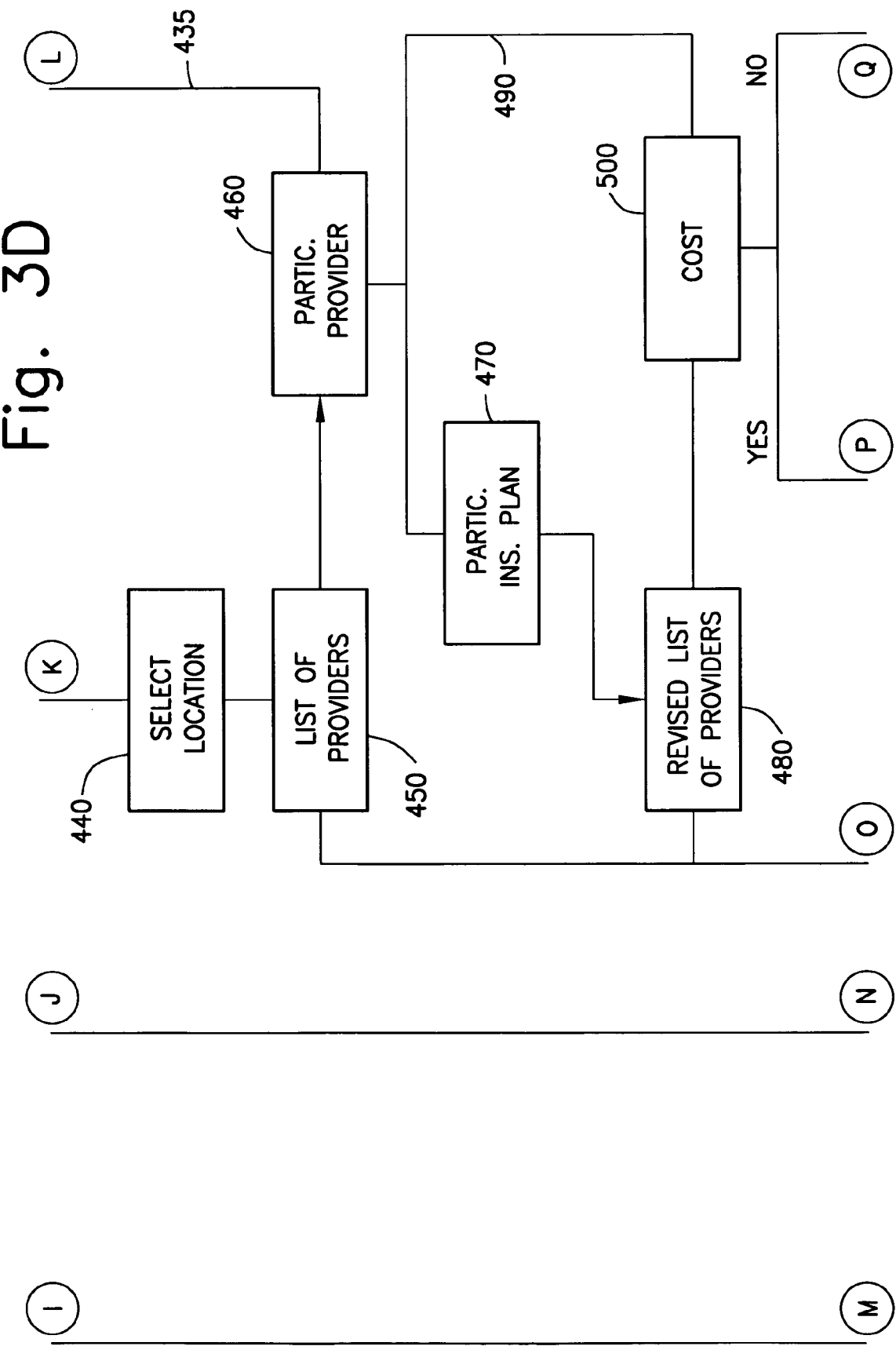
Figure 3F:
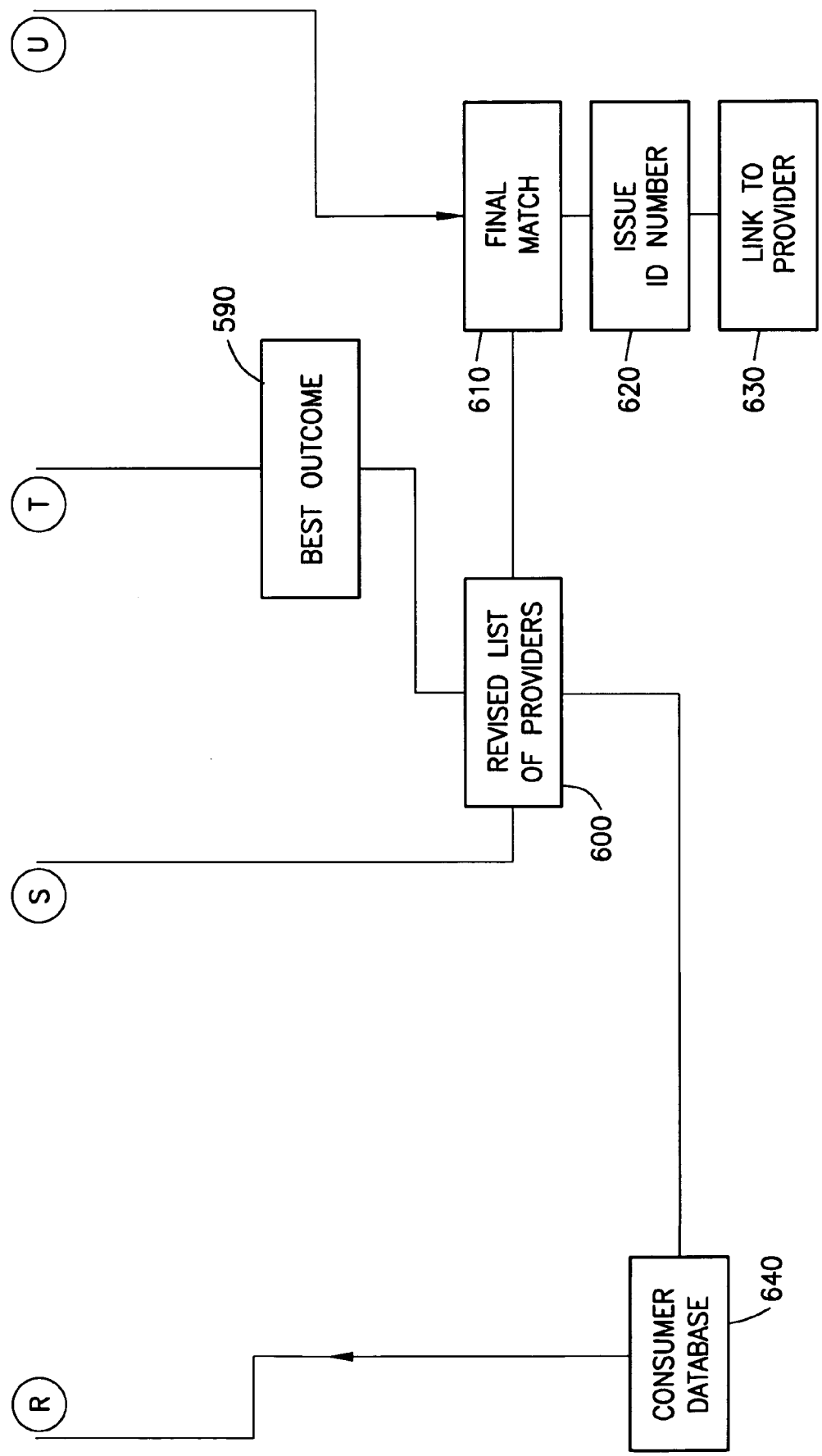

FIG. 3 shows a flow chart for software implementing the invention which is present, for example, at a network server.

With reference to FIG. 3, a consumer/provider of medical services logs onto the system by, for example, accessing the Internet using a home computer and an Internet service provider and entering the appropriate site address to access the network server. This is shown by START block 101. Once the user has accessed the server, the user will be provided with an appropriate set of computer screen displays to enable the user to interact with the system. The software for the system is generally shown in FIG. 3. The software includes a provider side P and a consumer side C. The provider side includes a number of data bases 100 including a provider data base 110. A registration fee program (by which providers register to participate in the program by providing necessary information about their medical products, facilities, etc. and preferably, pay a fee to participate) is also preferably provided. Other data bases include general demographics data base 130, a products data base 140, a code data base 150, and other data bases 160, as necessary. In addition, a data base 165 for multi disciplinary therapies, complementary and/or alternative medical regimens, e.g., pain management, physical therapy, acupuncture, etc. may be provided. Data base 165 can be combined into data base 150, particularly if a descriptive system for identifying medical products is employed, as described below. Further, a data base 170 containing information about what is included in connection with a particular medical service, designated "products" herein, an experience data base 180 related to the participating providers' experience with respect to certain medical products and an outcomes data base indicating the outcomes of the providers with respect to different courses of treatment, i.e., percentage of outcomes that were successful, are also provided. Also included is a price and capacity data base 200 indicating the price for the different included medical services and the capacity of the provider to perform those services, for example, the number of products that the provider can handle in a given time period. All of these data bases described are part of an overall provider data base 210.

Preferably, individual patients are not allowed direct access to the database without stepping through the consumer side C program flow to be described, but are only granted access at the appropriate point in the consumer side program flow. However, this preferred implementation does not preclude an implementation in which individual patients are allowed direct access to the database. Preferably, corporate consumers such as medical service providers, insurers, doctors, etc., would be allowed direct access to the databases, for purposes of, for example, registering as a participant and updating the database.

Although a data base 150 for medical codes, e.g., DRG, CPT codes, is shown, the system need not operate according to these codes. The codes are shown herein as one method to implement the system, primarily because the codes are well known and utilized extensively, and therefore are a convenient way of organizing the various medical products. However, the system could operate without using these well known codes and could operate, for example, using a descriptive type search engine or by using both code and descriptive techniques.

Price data base 200 can also be tiered to implement a price formula which varies based on volume. For example, a high usage consumer can get the benefit of a lower price structure based on the higher level of usage.

Turning now to the consumer side C, when the consumer 220 logs onto the system, a determination is first made whether the consumer is an actual patient 230 or a corporate consumer 240, for example, a medical insurer. If an individual patient, at 250 a determination is made as to whether the patient has a diagnosis for a medical condition. If the answer is "Yes", as shown at 260, the diagnosis is converted to a medical code, for example a DRG (diagnosis related group) code, as shown at 310. If the patient does not have a diagnosis, as indicated at 270, two options are presented. A link can be made to a data base (280) thereby to obtain a diagnosis 290, or a referral to a doctor can be made at 300 by allowing the patient to obtain a diagnosis 290 from a physician. In either case, the diagnosis is converted into the code shown at 310. If a code cannot be obtained, an exit is made from the system at 320. Alternatively, the system could operate without codes, and instead utilize a descriptive system, e.g., hernia, appendectomy, etc.

If the consumer is a corporate consumer 240, the corporate consumer preferably may be required to register and pay a fee, as indicated at step 245 in order to proceed further. Assuming the corporate consumer has a diagnosis for the particular patient about whom the inquiry is being made, the flow is to block 290.

Once an acceptable code for the necessary treatment is obtained, the system accesses a treatment data base 340. The treatment data base determines if there is only one option for treatment at 350. If so, indicated at 360, a code may be established at 370, for example, without limitation, a CPT 4, DRG or APC code. Like the provider side P, it is not necessary to use these medical codes, but they may be employed, as shown, because they are convenient and well known. Alternatively, more descriptive means can be employed. If there are multiple treatment options, as indicated at 380, the data base will indicate to the consumer the different medical options (390). The consumer then has the option of choosing a treatment as indicated at 400 or seeking a referral as shown at 410 which will then allow the choice of treatment to be made at 400. Once a treatment is chosen, the treatment is converted to a code (370), for example, a CPT 4 code, or descriptor. Once the code has been obtained (or other alternative description is obtained) treatment preferences are then determined beginning at 420. The treatment preferences can include such things as geography, whether there is a participating insurer, the cost of the treatment, the provider's experience with the particular treatment, i.e., how much volume the provider performs of the particular treatment, and the outcome of the treatment. Preferably, at step 420, the consumer is shown the various preference options and has the ability to prioritize them, in which case the information from the data bases will be provided based on the selected priority. At step 425, the system inquires as to the anticipated volume of the medical products desired by the consumer. If a large volume is requested, for example, certain providers may not have adequate capacity. Further, the volume will be taken into account in arriving at a cost for the product.

As shown in FIG. 3, if the geographical location of the provider is important to the consumer with respect to the medical treatment, as indicated at 430, the consumer selects the appropriate convenient location as indicated at 440. This allows a list of providers to be obtained, i.e., those providers who are convenient geographically to the consumer. This is indicated at 450. If geographical location is not a concern, flow is along line 435. The next step is a determination made based upon the consumer's insurance plan. This is indicated at 460. A determination is made at 460 if the consumer's insurance plan participates in the plan. This is indicated at 470. This will provide for a further revised list of providers who participate in the consumer's insurance plan as indicated at 480. If an insurer is not involved, or a participating insurer is not involved, the system proceeds along the line indicated by 490.

Next, a determination is made as to whether cost is a factor. This is indicated at 500. If cost is a factor, the provider offering the best price is determined at 510, leading to a further revised list of providers 520. If cost is not a factor, then line 530 is followed.

Following the determination with respect to the price, a determination is made as to whether the provider's experience with the treatment is important. This is indicated at 540. If Yes, the provider or providers in the revised list of providers 520 is determined that has the most experience with the treatment. This is indicated at 550. If experience is not a factor, then line 560 is followed. Assuming experience is a factor, a revised list of providers is determined at 570.

Next, as shown in the embodiment illustrated in FIG. 3, a determination is made as to whether outcome and/or consumer satisfaction is significant. Outcome and consumer satisfaction refers to the various providers' outcomes and consumer satisfaction with respect to the particular course of treatment, i.e., was the outcome successful or not, and/or was the consumer satisfied, as determined by the percentage of successful outcomes and/or consumer satisfaction. This is shown at 580 in FIG. 3. Assuming outcome/satisfaction is important, the provider or providers having acceptable outcomes are determined at 590 and a revised list of providers 600 based upon all the above factors is determined. Finally, at 610, a final match based upon the revised list of providers is determined at 610. The final match may be one or may be a number of providers who meet the criteria. At 620 an identification number is provided to the consumer and a link to the appropriate service provider determined by the final match 610 is provided at 630.

Although the various treatment preferences were shown in a particular order in FIG. 3, those preferences can be rearranged in a different order based on the consumer's preference, i.e., the consumer's prioritization of the preferences. If the prioritization is different, the program flow will accordingly be different.

A consumer data base 640 may also be developed based upon the revised list of providers and the various factors which determined the revised list of providers 600. Analysis of the consumer data base 640, particularly the priorities of the various consumers in selecting a provider, can then be fed back to the data bases 100 to incorporate this analysis into the data collected by the data bases 100. For example, customer satisfaction surveys can be conducted on line, and the results of the surveys added to the provider data base.

Accordingly, the system provides a method and apparatus for a consumer of health care services to be matched to an appropriate health care service provider via a computer link to a communications network such as the Internet.

Although the present invention has been described in relation to particular embodiments thereof, many other variations and modifications and other uses will become apparent to those skilled in the art. The present invention therefore, should be limited not by the specific disclosure herein, but only by the appended claims.

What is claimed is:

1. A system to match a consumer of health care services to a health care service provider over a communications network, the system comprising:
   at least one computer terminal associated with the consumer for allowing the consumer access to the communications network;
   a network server coupled to the communications network, the server comprising a computer program having:
   a service provider data base identifying a plurality of health care service providers and a plurality of medical service associated health care service products offered by the service providers;
   a first software portion for
   receiving a diagnosis provided by at least one of a consumer and an alternative diagnosis determiner and
   automatically determining at least one treatment option based on the received diagnosis provided by the consumer or determined by the alternative diagnosis determiner; and
   a second software portion for
   allowing the consumer to select a treatment from the at least one treatment option and
   automatically determining at least one appropriate service provider for the selected treatment, based on the selected treatment and further based on a treatment preference, the treatment preference comprising at least one of:
   geographical location of the provider,
   insurance plan participation,
   cost,
   provider experience with the at least one treatment option and
   provider outcome with respect to the at least one treatment option.

2. The system of claim 1, wherein the service provider data base comprises information related to a plurality of service providers, medical products offered by each provider, the provider's experience with each medical product, outcome of each provider with respect to each product, price for each product, description of each product and demographic location of each provider.

3. The system of claim 1, further wherein the first software portion automatically determines the number of treatment options based on the diagnosis.

4. The system of claim 3, wherein the first software portion allows selection of treatment options if more than one treatment option is available.

5. The system of claim 1, wherein the alternative diagnosis determiner comprises one of a link to a medical diagnosis database and a referral to a physician.

6. The system of claim 4, wherein the first software portion accesses the service provider database to describe the treatment option when more than one treatment option is available.

7. The system of claim 6, wherein the first software portion allows the consumer to obtain a referral to a physician to assist in understanding of treatment options.

8. The system of claim 1, wherein, after the consumer is matched to a service provider, an identification number is issued.

9. The system of claim 8, further comprising a link to the service provider.

10. The system of claim 1, further comprising a consumer data base obtained from the second software portion comprising information related to the consumer's choice of service provider.

11. The system of claim 10, wherein the consumer database is coupled to the service provider data base for updating the service provider data base.

12. The system of claim 1, wherein the second software portion has an input from the service provider data base to determine the at least one appropriate service provider.

13. The system of claim 1, wherein provider outcome includes an indication of consumer satisfaction.

14. The system of claim 1, further wherein the cost treatment preference includes the capability to offer a reduced cost for greater usage.

15. The system of claim 1, further comprising the capability to prioritize the treatment preferences in a selected order.

16. The system of claim 1, further comprising a program flow for charging the consumer a fee to participate in the system.

17. A method to match a consumer of health care services to a health care service provider over a communications network, the method comprising:
   allowing the consumer to access the communications network to connect to a network server coupled to the communications network, the server comprising a computer program having a service provider data base identifying a plurality of health care service providers and a plurality of medical service associated health care service products offered by the service providers;
   receiving a diagnosis provided by at least one of a consumer and an alternative diagnosis determiner;
   automatically determining with the computer program at least one treatment option based on the received diagnosis provided by the consumer or determined by the alternative diagnosis determiner;

allowing the consumer to select a treatment from the at least one treatment option; and automatically determining with the computer program at least one appropriate service provider for the selected treatment, based on the selected treatment and further based on a treatment preference, the treatment preference comprising at least one of geographical location of the provider, insurance plan participation, cost, provider experience with the at least one treatment option, and provider outcome with respect to the at least one treatment option.

18. The method of claim 17, wherein the service provider data base comprises information related to a plurality of service providers, medical products offered by each provider, the provider's experience with each medical product, outcome of each provider with respect to each product, price for each product, description of each product and demographic location of each provider.

19. The method of claim 17, further wherein the first step of automatically determining comprises automatically determining the number of treatment options based on the diagnosis.

20. The method of claim 19, where the first step of automatically determining allows selection of a treatment option if more than one treatment option is available.

21. The method of claim 17, wherein the alternative diagnosis determiner comprises one of a link to a medical diagnosis database and a referral to a physician.

22. The method of claim 20, wherein the first step of automatically determining comprises accessing the service provider database to describe the treatment option when more than one treatment option is available.

23. The method of claim 22, wherein the first step of automatically determining allows the consumer to obtain a referral to a physician to assist in understanding of treatment options.

24. The method of claim 17, further comprising, after the consumer is matched to a service provider, issuing an identification number.

25. The method of claim 24, further comprising providing a link to the service provider.

26. The method of claim 17, further comprising generating a consumer data base comprising information related to the consumer's choice of service provider.

27. The method of claim 26, wherein the consumer database is coupled to the service provider data base for updating the service provider data base.

28. The method of claim 17, further comprising providing an input from the service provider data base to enable said second step of determining to determine the at least one appropriate service provider.

29. The method of claim 17, wherein provider outcome includes an indication of consumer satisfaction.

30. The method of claim 17, further wherein the cost treatment preference includes the capability to offer a reduced cost for greater usage.

31. The method of claim 17, further comprising the capability to prioritize the treatment preferences in a selected order.

32. The method of claim 17, further comprising charging the consumer a fee to participate.

33. A computer readable storage medium for a program for operating a system to match a consumer of health care services to a health care service provider over a communication network coupling at least one computer terminal associated with the consumer for allowing the consumer access to the computer network and a network server, the computer readable storage medium comprising a computer program comprising:

a service provider data base identifying a plurality of health care service providers and a plurality of medical service associated health care service products offered by the service providers;

a first software portion for receiving a diagnosis provided by at least one of a consumer and an alternative diagnosis determiner and automatically determining at least one treatment option based on the received diagnosis provided by the consumer or determined by the alternative diagnosis determiner; and a second software portion for allowing the consumer to select a treatment from the at least one treatment option, and automatically determining at least one appropriate service provider for the selected treatment, based on the selected treatment and further based on a treatment preference, the treatment preference comprising at least one of:

geographical location of the provider, insurance plan participation, cost, provider experience with the at least one treatment option and provider outcome with respect to the at least one treatment option.

34. The storage medium of claim 33, wherein the service provider data base comprises information related to a plurality of service providers, medical products offered by each provider, the provider's experience with each medical product, outcome of each provider with respect to each product, price for each product, description of each product and demographic location of each provider.

35. The storage medium of claim 33, further wherein the first software portion automatically determines the number of treatment options available based on the diagnosis.

36. The storage medium of claim 35, wherein the first software portion allows a selection of treatment options if more than one treatment option is available.

37. The storage medium of claim 33, wherein the alternative diagnosis determiner comprises one of a link to a medical diagnosis database and a referral to a physician.

38. The storage medium of claim 36, wherein the first software portion accesses the service provider database to describe the treatment option when more than one treatment option is available.

39. The storage medium of claim 38, wherein the first software portion allows the consumer to obtain a referral to a physician to assist in understanding of treatment options.

40. The storage medium of claim 33, wherein, after the consumer is matched to a service provider, an identification number is issued.

41. The storage medium of claim 40, further comprising a link to the service provider.

42. The storage medium of claim 33, further comprising a consumer data base obtained from the second software portion comprising information related to the consumer's choice of service provider.

43. The storage medium of claim 42, wherein the consumer database is coupled to the service provider data base for updating the service provider data base.

44. The storage medium of claim 33, wherein the second software portion has an input from the service provider data base to determine the at least one appropriate service provider.

45. The storage medium of claim 33, wherein provider outcome includes an indication of consumer satisfaction.

46. The storage medium of claim 33, further wherein the cost treatment preference includes the capability to offer a reduced cost for greater usage.

47. The storage medium of claim 33, further comprising the capability to prioritize the treatment preferences in a selected order.

48. The storage medium of claim 33, further comprising a program flow for charging the consumer a fee to participate.

* * * * *